United States Patent [19]

Vierstra et al.

[11] Patent Number: 5,773,705
[45] Date of Patent: Jun. 30, 1998

[54] UBIQUITIN FUSION PROTEIN SYSTEM FOR PROTEIN PRODUCTION IN PLANTS

[75] Inventors: Richard David Vierstra; David Hondred, both of Madison, Wis.; Judy Callis, Davis, Calif.

[73] Assignee: Wisconsin Alumni Research Foundation, Madison, Wis.

[21] Appl. No.: 450,834

[22] Filed: May 25, 1995

Related U.S. Application Data

[63] Continuation of Ser. No. 999,709, Dec. 31, 1992, abandoned.

[51] Int. Cl.$^6$ .............................. A01H 1/04; C12N 5/00; C12N 15/00
[52] U.S. Cl. ..................... 800/250; 800/205; 435/69.1; 435/69.7; 435/172.3; 435/320.1; 435/419; 536/23.4; 536/23.6; 935/35; 935/61; 935/67
[58] Field of Search ................................. 435/69.1, 69.7, 435/172.3, 240.4, 320.1; 536/23.6, 23.4; 800/205, 250; 935/9, 35, 60, 67

[56] References Cited

PUBLICATIONS

AS Moffatt (1992) Science 255:25.
EA Sabin et al. (1989) Bio/Technology 7:705–709.

*Primary Examiner*—Bruce R. Campell
*Attorney, Agent, or Firm*—Quarles & Brady

[57] ABSTRACT

Ubiquitin is an abundantly expressed protein in all eukaryotic organisms. A gene for plant ubiquitin, isolated from *Arabidopsis thaliana*, has been used in a plant expression vector to produce a ubiquitin-protein fusion. Natural factors in the plant cleave such a fusion protein to release ubiquitin and the desired protein. It has been found that such fusions result in protein expression levels higher than those that can be obtained from expression of the protein alone.

8 Claims, 4 Drawing Sheets

UBIQUITIN FUSION PROTEIN SYSTEM FOR PROTEIN PRODUCTION IN PLANTS

This is a continuation of application Ser. No. 07/999,709 filed Dec. 31, 1992 now abandoned.

FIELD OF THE INVENTION

The present invention relates to the field of plant genetic engineering in general and relates, in particular, to improve techniques and vectors for the increased production of heterologous proteins in transgenic plants.

BACKGROUND OF THE INVENTION

Within the past decade significant progress has been made in the general field of plant biotechnology. Plant scientists have developed the ability to transfer into crop plants foreign genes which can express proteins of foreign origin. Some genes transferred into plants are intended to express proteins intended to confer beneficial agronomic traits to transgenic plants, such as resistance to pathogenic organisms or varying the morphological characteristics of the plants. It is now also contemplated that plants may be used for the economic manufacture of industrial and pharmaceutical proteins. While commonly in the past, industrial and pharmaceutical proteins have been expressed in bacterial or microbial expression systems, there are certain advantages to the production of proteins in plants that suggest that protein production in plants will become commercially attractive for certain proteins needed in quantity. On a weight basis, plant proteins can be produced more economically than protein production systems requiring industrial fermenters or tissue culture systems. Also plant seeds, in particular, have inherent mechanisms favorable to protein stability, and thus offer the prospect that proteins can be easily stored until needed in the seed from transgenic plants. Expressing foreign proteins in plants has generally become possible, at least for most proteins, but typically the yield of protein produced in the transgenic plants is rather limited. In an attempt to overcome the limited expression of foreign proteins in plants, various techniques have been utilized to enhance expression levels. Such techniques include selection of stronger promoters, the use of untranslated transcriptional enhancing sequences, and various other sequences intended to enhance the level or the stability of proteins produced in plants.

The protein ubiquitin is perhaps one of the most conserved proteins among eukaryotic life forms and is found in all eukaryotes. Ubiquitin consists of a compact globular core with a flexible, protruding carboxyl terminus. The amino acid sequence of ubiquitin thus far seems invariant among all higher plant species examined and differs in a fairly modest number of residues from corresponding ubiquitin proteins in animals and eukaryotic microorganisms. Ubiquitin is often found covalently attached as a fusion to other cellular proteins by an isopeptide linkage between the residue at the carboxy-terminus of ubiquitin and lysine residues within other proteins. Ubiquitin-protein fusions or conjugates have been identified to have several possible fates in the plant cell. The best understood fate is a ubiquitin-dependent degradation pathway through selective proteolysis. As a part of that degradation process, a proteosome-related protease completely degrades the target protein and, in turn, releases functional ubiquitin to be recycled. Certain forms of ubiquitin-protein conjugates are also known to be stable. The function of these stable forms is unknown, although it is possible they have a regulatory function.

Ubiquitin is unusual among eukaryotic proteins in that it is encoded by a multi-gene family of genes which include members having natural gene repeats. In this case, a peptide bond links the residue at the carboxy terminus of one ubiquitin to the amino terminus of the next ubiquitin. The natural ubiquitin gene repeats include several repeated regions encoding identical, or nearly identical, amino acid sequences, even if the DNA sequences of the repeats vary to some degree. To generate free ubiquitin monomers from such fusions, plants contain activities that specifically digest the bond between adjacent ubiquitin repeats.

Artificial ubiquitin fusion proteins have been constructed for other host systems, to express and accumulate foreign proteins, notably in yeast and *E. coli*. Those systems involved expressing proteins as carboxyl terminal fusions to ubiquitin and was demonstrated to increase the yields of several recalcitrant proteins, up to increases of several hundred fold over that which could be obtained in other systems. Although there is significant conservation among ubiquitin proteins, it was determined that the ubiquitin sequences for yeast were unsuitable for use in plants, due to an unexpected toxicity, in spite of the fact that the yeast amino acid sequence is only three residues different from the plant sequence.

SUMMARY OF THE INVENTION

The present invention is summarized in that a ubiquitin fusion protein vector system is described which enables the enhanced expression of a foreign protein produced in a transgenic plant system.

The present invention is also summarized in that plants expressing ubiquitin-protein fusions are described, which are useful vehicles for producing peptides or proteins of industrial or pharmaceutical interest in quantity.

It is an object of the present invention to provide a system for the efficient expression of heterologous proteins in transgenic plants and to enable the production in transgenic plants of proteins which have been heretofore recalcitrant of efficient expression in transgenic plants.

It is a feature of the present invention that the ubiquitin fusion proteins created through this process will naturally be cleaved by factors natively present in plant cells, so as to release both the ubiquitin and the protein desired.

It is a further feature of the present invention in that the stability of the resulting protein can also be modified through the use of a selective amino acid modification at the amino terminus of the ultimate mature protein which is created by the fusion protein technology described herein.

Other objects, advantages and features of the present invention become apparent for the following specification when taken in conjunction with the accompanying drawings.

DETAILED DESCRIPTION OF THE INVENTION

The present invention is directed to the production of desired proteins in plants through a strategy involving the construction of expression cassettes for those proteins which include a region coding for an amino terminal fusion of a ubiquitin protein to the protein of interest. The fusion protein is cleaved by native plant enzymes to release ubiquitin and the desired protein. The use of the ubiquitin-protein fusion strategy for production of the desired protein results in a higher level of expression of the protein than can be achieved without the ubiquitin fusion technique. This strategy thus lends itself to the creation of proteins in transgenic plants of both agronomic and industrial interest.

Figure 1:
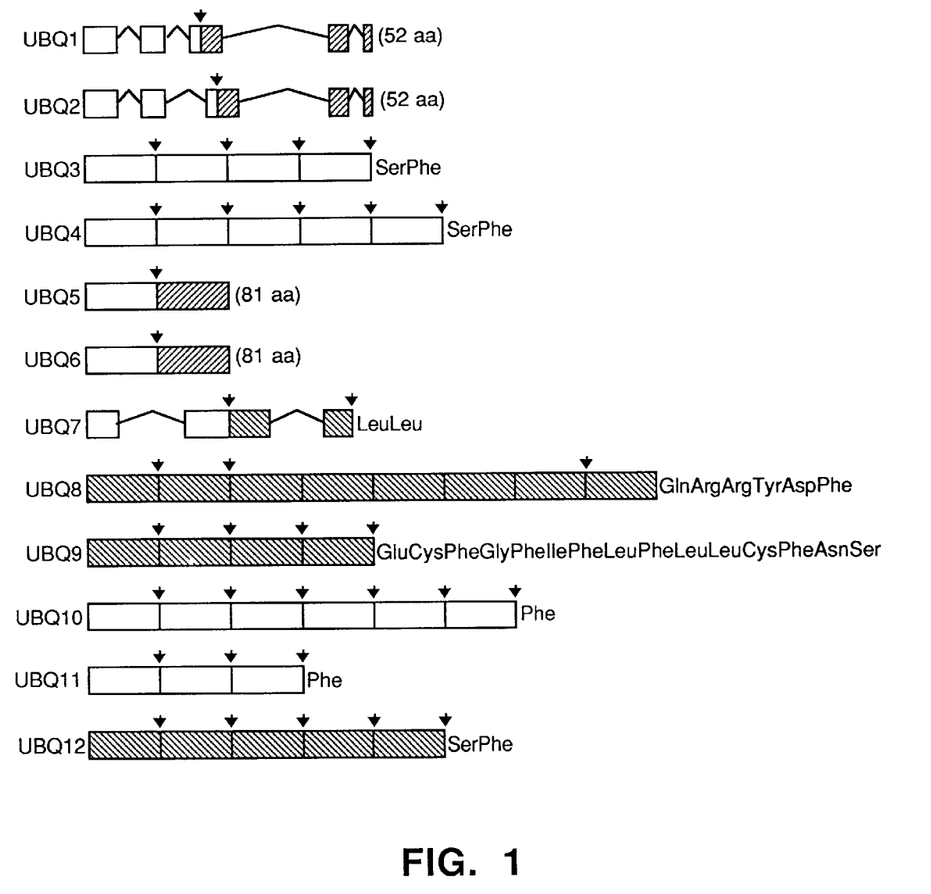
FIG. 1 is a chart illustrating the nature of the ubiquitin genes from Arabidopsis which have been identified.

The investigators here have studied the ubiquitin gene family in plants and have identified twelve different ubiquitin fusion genes present in the genome of Arabidopsis thaliana. From those twelve ubiquitin fusion genes normally present in the plant, the analysis of the investigators revealed that the genes fell into three classes. FIG. 1 schematically illustrates the ubiquitin genes so as to show relationships between the Arabidopsis ubiquitin fusion genes. One class of genes, including the genes designated UBQ3, UBQ4, UBQ10, and UBQ11, is the polyubiquitin genes. Each polyubiquitin gene includes two or more repeats of the same 228 base pair ubiquitin coding region which are contiguously linked. While the DNA sequence of the repeats varies somewhat, the amino acid sequences which they encode are virtually identical. The last repeat of each gene of the polyubiquitin genes includes one or several additional amino acids linked to the carboxyl-terminus glycine. The number of repeats varies within the various polyubiquitin genes. The four Arabidopsis polyubiquitin genes contain 3, 4, 5, and 6 ubiquitin repeats. Other organisms are known to have varying levels of different polyubiquitin genes with varying numbers of repeats.

The second class of ubiquitin genes, including genes UBQ1, UBQ2, UBQ5 and UBQ6, encode a ubiquitin monomer followed by one of two unrelated extension peptides which are ribosomal proteins. The third class of ubiquitin genes, including genes UBQ7, UBQ8, UBQ9, and UBQ12, encode genes similar in structure to the polyubiquitin genes, but which synthesize proteins which are only 85 to 90% identical to the consensus ubiquitin sequence. In fact, whether these genes are truly expressed in Arabidopsis, or merely represent pseudogenes, is still unknown.

The investigators here have characterized the sequence, at both an amino acid and DNA level, of the varying polyubiquitin genes isolated from Arabidopsis. Based on that analysis, the investigators then chose one of the repeat ubiquitin sequences for use as a candidate in a ubiquitin fusion protein expression system. The portion that was chosen was the last of the three repeats within the Arabidopsis UBQ11 polyubiquitin gene. This particular ubiquitin repeat was chosen because its coding region, at the nucleotide level, is at least 80 to 95% identical to that of each of the other repeats within the polyubiquitin family of genes, and was 100% identical at the amino acid level to all the expressed ubiquitin coding regions in Arabidopsis. Thus, this gene was selected as a pseudo-consensus gene amongst all the ubiquitin repeat segments within the polyubiquitin genes. Various genetic manipulations were then undertaken with this gene to facilitate its use in a plant expression vector, and so that a desired protein coding sequence could be conveniently inserted 3' to the gene encoding the ubiquitin segment, to enable improved expression of that protein in plants.

The advantage of using the ubiquitin fusion protein approach, as a methodology for expressing proteins in plants, is based on the abundance of the ubiquitin protein both in plant and animal cells, and the suggestion raised by that fact that ubiquitin genes are highly expressed. Why synthesizing heterologous proteins as ubiquitin fusions augments their accumulation in plants, or other hosts, is yet unclear. The fusion vectors sequences do not seem to alter the sequences 5' and 3' of the coding regions, nor do the fusion vectors appear to effect the level of transcriptional efficiency. There is also evidence to suggest that differences in protein stability following processing may not be factor. It has been suggested that the favorable codon usage bias of ubiquitin may enhance subsequent translation of the appended coding regions. Another very plausible explanation is that the ubiquitin facilitates folding and stability of the following peptide chain. Ubiquitin has a highly stable 3-dimensional structure, making it resistant to harsh conditions and allowing it to refold easily following denaturation. It is also possible that ubiquitin could shield proteins from co-translational degradation. However, regardless of the methodology which results in the effect, the evidence now seems clear that the use of these ubiquitin fusion proteins will result in higher levels of protein expression than could be achieved by the expressing protein alone using comparable promoters and transformation techniques.

Figure 2:
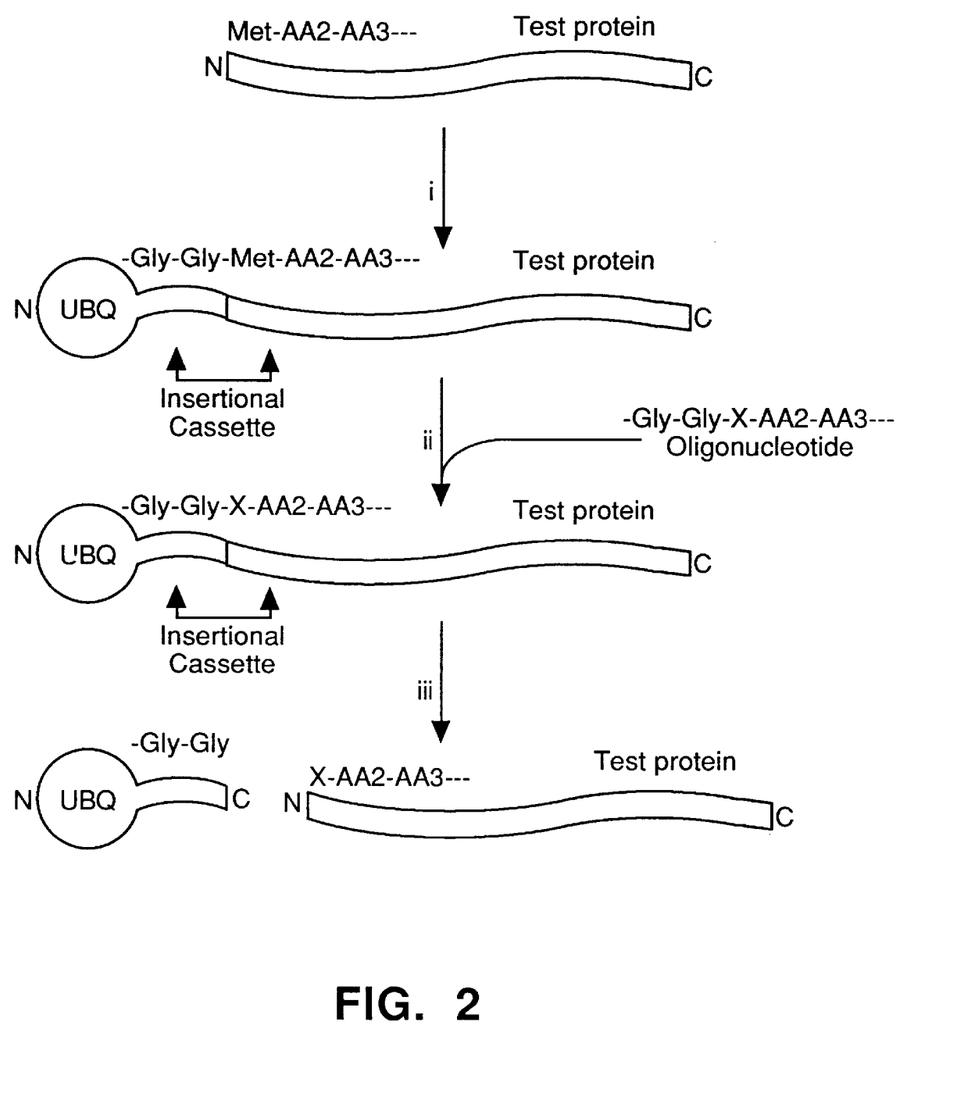
FIG. 2 is a schematic illustration illustrating the theory behind the expression of a ubiquitin-protein fusion.

The use of the ubiquitin-protein fusion strategy takes advantage of the normal plant biochemical mechanisms which are designed to cleave ubiquitin from the amino terminal end of any protein to which it is attached. Endogenous plant factors, notably by the ubiquitin-protein hydrolase enzyme, cleave ubiquitin-protein fusion specifically at the carboxyl-terminal glycine of ubiquitin, regardless of the subsequent amino acid sequence contained in the following protein. Thus, the ubiquitin-protein fusion gene causes expression of a fusion protein containing the ubiquitin gene at the amino terminus of the fused protein, subsequent processing promptly cleaves the ubiquitin region from the protein to be expressed, resulting in a mature protein free of ubiquitin. This process is illustrated in FIG. 2. Note that in joining the protein P to be produced in plants, the amino terminal end of the protein may be altered at the DNA level so as to not encode for methionine. This is because the amino terminal methionine is encoded by the ubiquitin portion of the fusion protein. In fact, the choice of the amino acid for the amino terminus of the mature protein may have a effect on protein stability of the ultimately desired mature protein in the transgenic plant. This would be true if the "N-terminal rule" divined for expression of ubiquitin-protein fusion in other hosts hold true for plants. This rule suggests that the choice of the amino terminal residue of the mature protein effects the level of protein which can be detected in the organism. In general, the choice of the amino acids methionine, valine, and alanine seem to stabilize the production of the protein, while a selection for the amino acids glutamine and arginine seem to destabilize the resulting protein. In any event, as also viewed in FIG. 2, the amino acid sequence at the future cleavage site, designated G-G-X-AA2-AA3, where AA2 and AA3 are the native amino acids of the desired protein, and the amino acid X represents the amino terminus of the protein to be expressed, can be readily seen. After expression, the ubiquitin-protein fusion is cleaved by the native plant enzymes between the second ubiquitin glycine and the amino terminal X residue of the protein, thus freeing the protein from the ubiquitin. The ubiquitin is naturally recycled within the cell.

Plant gene expression vectors can, and have been, constructed specifically to express such ubiquitin-protein fusions in plant cells. The improvement due to the ubiquitin-protein fusion strategy is believed independent of choice of promoter, or the choice of 3' polyadenylation or transcription termination sequence utilized in the expression cassette. The strategy described below details the incorporation of such a ubiquitin fusion sequence into an expression vector which can be utilized to express any protein that is desired.

The construction of plant expression vectors must be adapted for use with plant transformation procedures for transferring those vectors into transgenic plants. Several methods are now known for the introduction of foreign genes into plants to create stably transformed and expressing transgenic plants. These methods include plant transformation through use of the plant pathogen *Agrobacterium tumefaciens*, the use of accelerated-particle gene delivery techniques, and the use of electroporation, or electric shock, to introduce exogenous DNA into plant cells. Methodologies have been published which describe the stable germ-line transformation of most of the important crop species both dicot and monocot, including soybean, corn, cotton, rice, and wheat. It has also been previously demonstrated that foreign gene constructs, when genetically engineered into lines of plants, are thereafter stable and can be transferred to the progeny of the plants through normal mendelian inheritance. Furthermore, while each genetic transformation process involves a randomness in the insertion of the inserted DNA into the plant genome, and while there are strong position-related effects in the level of expression achieved through each plant line created through such genetic transformation, any given plant line remains stable in its expression characteristics and that stable pattern of plant gene expression is inherited by the progeny of that plant line.

It is anticipated that the plant gene expression cassette described in the specification would be useful with a wide variety of proteins to be produced in plants both for agronomic and industrial traits. As an example of proteins which might be usefully produced in plants for agronomic purposes, there are various proteins necessary for resistance either to chemical (e.g. herbicide) or biological threats to plant vigor. There are significant reports of successful efforts to express the delta endotoxin from *Bacillus thuringiensis* in plants to produce toxicity to target insects. A class of proteins known as thionins, which are present in the endosperm and leaves of various cereals, seems to have substantial toxicity toward bacteria, fungi, and insects, thereby suggesting a role in defense. These proteins might usefully be produced in plants through a technique like that described herein. A protein known as systemin, which is only 18 amino acids long and is therefore difficult to produce in plants, is believed to be the systemic plant signal for defense against insect predation. The use of the fusion protein strategy described herein enables the production of smaller amino acids that might be otherwise difficult to produce in plants. A similar class of short proteins is cecropins, which are known to have strong bactericidal activity. Many of the industrial proteins which have heretofore been produced in plants are used for research or industrial exploration of plant expression systems. Such proteins would include phytochrome and luciferase which are both useful markers systems for investigating plant expression systems. It is also anticipated that proteins of pharmaceutical interest, such as growth factors, lymphokines, hormones and activators, can also be abundantly produced in plants using the ubiquitin protein fusion strategy.

It is anticipated that the enhanced level of expression achieved by the ubiquitin-protein fusion strategy is independent of the species of plant. All plants are believed to abundantly express similar ubiquitin gene families. While the controlled comparison experiments described in the example below have so far only been conducted in the usual model plant genetic engineering species, tobacco, other ubiquitin protein fusion genes have also been successfully transformed into rice and are expressing. The strategy is believed generally suitable for all crop species, dicots and monocots alike.

Set forth below in the UBQ11 third repeat DNA sequence (SEQ ID. NO: 1). This UBQ11 third repeat has a carboxyl terminus phenylalanine residue not present in other ubiquitins, which is encoded by the 3' "TTC" of SEQ ID. NO. 1. Using this sequence, by oligonucleotide construction, one can construct a synthetic ubiquitin repeat gene for use in constructing ubiquitin-protein fusion genes for insertion in plants. Alternatively, this same sequence may be used to synthesize probes for recovering cDNA or genomic gene sequences from Arabidopsis, or other plants. Once the ubiquitin encoding sequence is available, the construction of a plant expression vector can proceed using other necessary gene sequences (e.g. promoters and termination sequences) readily available to those of ordinary skill in the art.

EXAMPLES

The work described in these examples involves the construction of a ubiquitin fusion protein based on the third repeat of the UBQ11 gene. The example was performed utilizing genes and promoters which are otherwise well characterized, in order to help identify the contribution of the ubiquitin fusion protein to the total expression achieved by the cassette.

The UBQ11 ubiquitin coding sequence was isolated, cloned, and sequenced by the investigators here. The DNA sequence for the UBQ11 gene (with the phenylalanine codon) is presented in Sequence ID. No. 1 below. The work also made use of two previously existing plant expression vectors which were graciously made available to the investigators here. The first was a gene expression cassette designated pAMVBTS, which is a functional plant expression cassette including the Cauliflower Mosaic Virus 35S promoter (CaMV 35S), a 5' non-translated leader sequence derived from the alfalfa mosaic virus (AMV leader), and a coding region containing a truncated portion of the lepidopteran-specific *Bacillus thuringiensis* delta endotoxin (B.t. toxin). The other vector which was made available to the investigators was a plasmid designated pCMC1100 which included, among other important sequences, a gene encoding the enzyme β-glucuronidase (GUS), followed by a polyadenylation or transcriptional termination region derived from the nopaline synthase gene from *Agrobacterium tumefaciens* (Nos polyA). The GUS gene is a convenient test gene for protein expression since its expression can readily be detected, and quantitated, by histochemical assay for enzyme activity. All of the protein coding sequences, the CaMV 35S promoter, and the Nos terminator, were used in the work described below.

Figure 3:
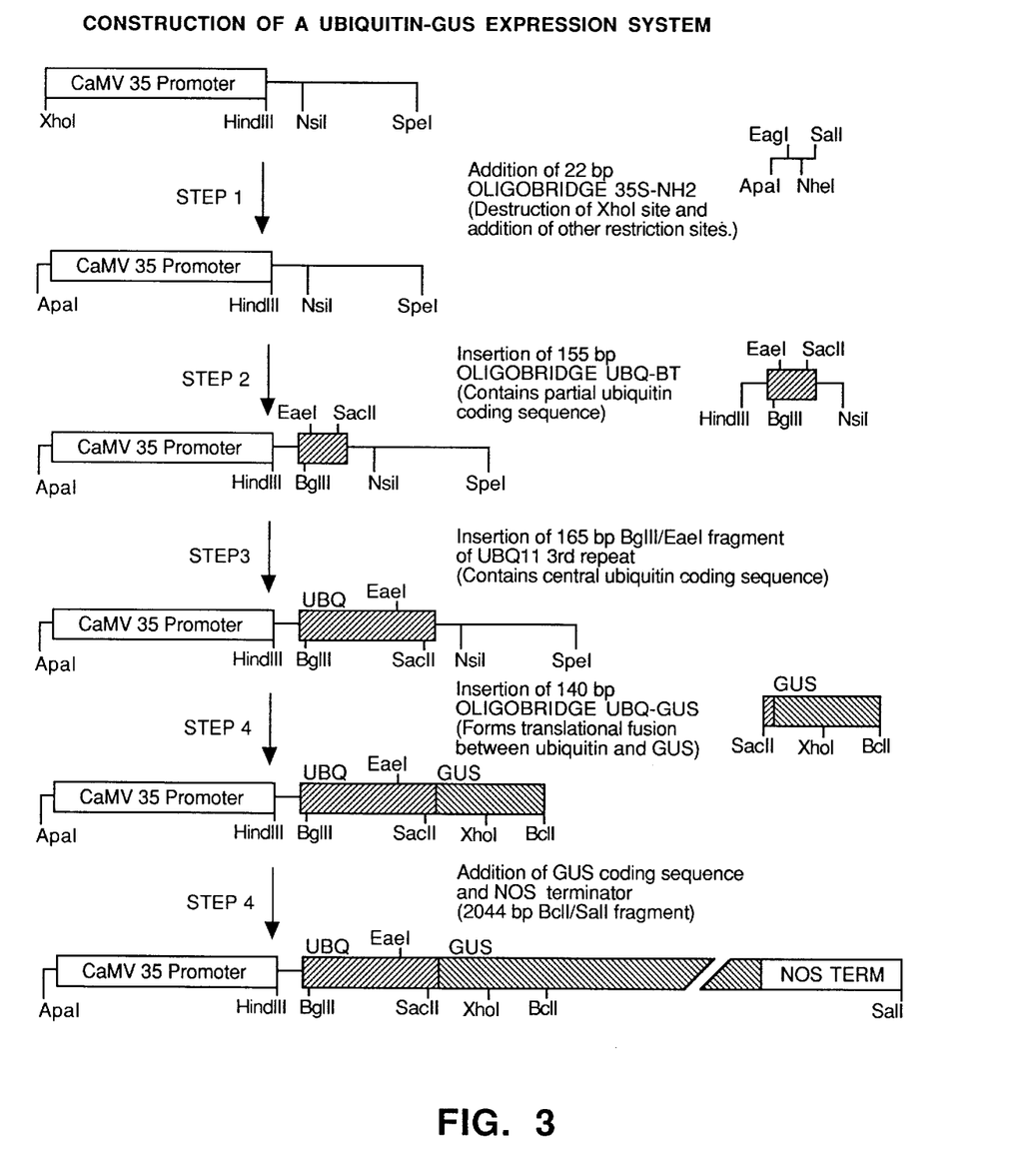
FIG. 3 is a schematic illustration illustrating some of the DNA manipulations performed in creating a fusion protein expression vector in accordance with the present invention.

Illustrated in FIG. 2 is the general strategy for the construction of the ubiquitin-protein fusion plant expression vector. The CaMV 35S promoter, well known as a highly expressing constitutive promoter in plant systems, together with the AMV RNA leader sequence, was obtained by a double digestion of the pAMVBTS plasmid with Xho I and Spe I restriction endonucleases, followed by isolation of a resulting 645 base pair fragment. The Xho I restriction site was destroyed, and new restriction enzyme recognition sites (Apa I, Eag I, Nhe I) were introduced 5' to the CaMV 35S promoter in the following manner. The CaMV 35S promoter was digested with Xho I and Spe I restriction enzymes, was purified, and was ligated with a 22 base pair oligonucleotide designated Oligobridge 35S-NH2, as set forth in Sequence ID. No. 2 below. Notice that in SEQ ID. NO. 2 that one DNA strand is 22 nucleotides while the other strand is 14 nucleotides. This was intentionally done to leave overhanging ends for the ligation. This step, illustrated at 11 in FIG. 3, was performed to generate a promoter containing fragment that could be conveniently manipulated during subsequent cloning steps.

The plasmid containing the promoter, now followed by the additional restriction sites, was subsequently digested with Hind III and Nsi I restriction enzymes. Another oligonucleotide, designated Oligobridge UBQ-BT, and set forth in Sequence ID. No. 3 below, was similarly digested to yield a 155 base pair fragment. The 155 base pair UBQ-BT bridge fragment was ligated to the CaMV 35S promoter fragment as indicated at step 2 in FIG. 3. This sequence now included, at its 3' end, the appropriate DNA sequence so that a ubiquitin coding sequence could be added after the promoter. The oligonucleotide UBQ-BT contained 10 base pairs of the ubiquitin 5' coding sequence, ending at the Bgl II restriction site, and also contained 50 base pairs of the ubiquitin 3' coding sequence, beginning at the Eae I restriction site contained within the oligonucleotide. The oligonucleotide bridge UBQ-BT was designed so that a translationally silent Sac II restriction site would be engineered into the 3' end of the ubiquitin coding sequence, as indicated after Step 2 in FIG. 3. The native UBQ11 third repeat nucleotide sequence was modified in the oligonucleotide so that the restriction enzyme Sac II now recognizes the site indicated, but the amino acid sequence encoded by the DNA remains the same as in the native ubiquitin monomer.

During the cloning and sequencing of the ubiquitin genes, a UBQ11 cDNA subclone was obtained which contained the third repeat of the UBQ11 native gene fragment. A DNA fragment was released from the subclone, by digestion with the restriction enzymes Bgl II and Eae I to yield a 165 base pair fragment. Those two restriction enzyme recognition sites can be identified in SEQ ID. NO: 1 below. The coding sequence of the third repeat of the UBQ11 gene was then inserted in the expression vector by replacing the region between the Bgl II and Eae I restriction sites in the UBQ-BT fragment with the 165 base pair fragment from the UBQ11 cDNA clone. The resulting fragment, shown following step 3 in FIG. 3, now contained the CaMV 35S promoter followed by the complete amino acid coding sequence of the ubiquitin UBQ11 repeat sequence.

Next another oligonucleotide, designated Oligobridge UBQ-GUS, and set forth in SEQ ID. NO: 4 below, was created. The UBQ-GUS fragment was then digested with the restriction enzymes Sac II and Xba I to yield a 140 base pair DNA fragment. This 140 base pair fragment was then ligated to the 3' Sac II site of the ubiquitin coding sequence that had been engineered into the ubiquitin native gene sequence in the manner described above. This step is indicated at 4 in FIG. 3. An Xba I site existed in the polylinker of the plasmid being used. For convenience in understanding the gene manipulations which have occurred, a Sequence ID No. 5 is presented below which shows the assembled gene sequence created by the manipulations described above. The combined sequence thus created contains a Bcl I restriction site that allowed the coding sequence for GUS gene to be ligated, in reading frame, to the ubiquitin coding sequence 5' to it on the expression vector. SEQ ID. NO. 6 presents the amino acid sequence of ubiquitin. The carboxyl terminal phenylalanine codon from SEQ ID. NO. 1 was removed by subsequent manipulations to add the ATG codon for the second protein of the fusion.

The GUS coding sequence, together with its following polyadenylation sequence from nopaline synthase (Nos) was then purified as a 2044 base pair DNA fragment from the plasmid pCMC1100 by double digestion with Bcl I and Sal I. This 2.04 kilobase base pair fragment was then ligated to the 3' end of the UBQ-GUS oligonucleotide insert, to produce the expression system to synthesize the ubiquitin-GUS fusion protein under the control of the cauliflower mosaic virus 35S promoter. This is illustrated at step 5 in FIG. 3. The total size of the expression vector was approximately 2.8 kilobases in size and was flanked at the 5' end by the restriction enzyme recognition sites for Eco RI, Apa I, and Kpn I, all of which were obtained from the polylinker of the original host plasmid or were artificially inserted. At the 3' end, the vector was flanked by a Sal I restriction enzyme site located 3' to the Nos polyadenylation region.

A control expression vector was also made. This vector was identical in sequence to the ubiquitin-protein fusion expression system, except that it lacked the ubiquitin 5' coding region. An Oligobridge 35S-GUS was created to directly link the CaMV 35S promoter to the GUS coding region. The oligonucleotide 35S-GUS was digested with Hind III and Xba I and ligated to the Apa I and Hind III fragment containing the CaMV 35S promoter. This construction was subsequently digested with Bcl I and ligated to the 2.04 kilobase pair DNA fragment containing the GUS coding sequence in the NOS terminator.

The finished constructs were excised as a Kpn I and Sal I digestion fragments and ligated into the plant transformation vector Bin19, which has the T-DNA border sites for T-DNA transfer into Agrobacterium-mediated transformation protocols. Alternatively, the fragments were transferred into a vector for direct transformation into rice plants by accelerated-particle transformation techniques. The plants transformed through the Aarobacterium-mediated transformation system were tobacco plants. The accelerated particle transformation method has been used to transform rice plants.

Figure 4:
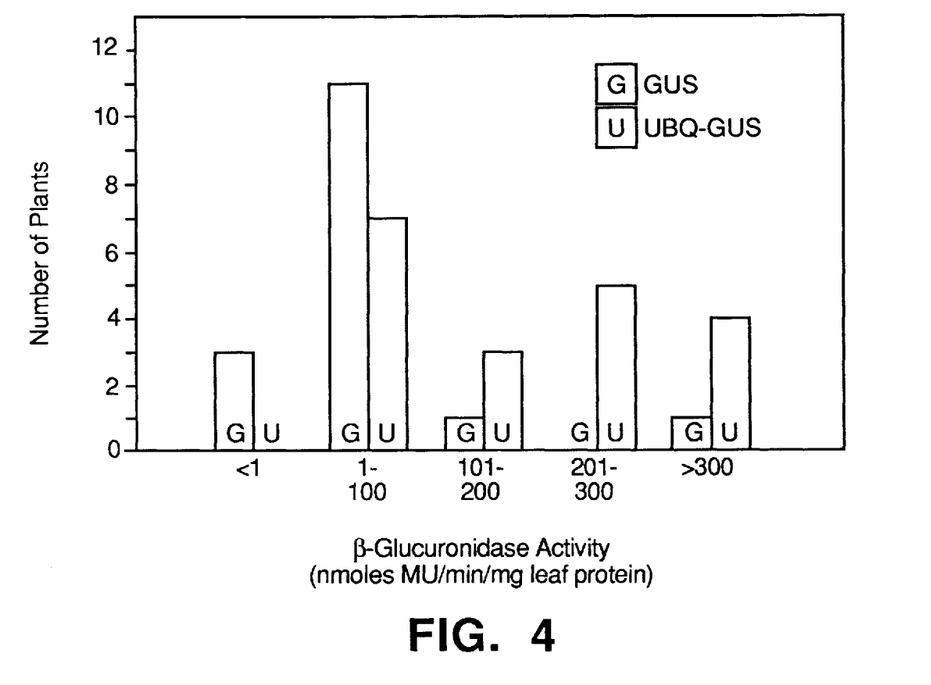
FIG. 4 is a graphical illustration of the protein expression characteristics of experimental and control plants from the example below.

The results of the protocols conducted in the Agrobacterium-mediated transformation of tobacco plants is illustrated generally in FIG. 4. As with all plant transformation experiments, a significant variation in expression in each given transgenic plant line was discovered. As is typical in such experiments, there is significant variation in the expression level due to positional effects in each plant line created, although that level of expression is characteristic for the line, and fully inheritable by mendelian inheritance by the progeny plants in the line. As an examination of the chart provided in FIG. 4 makes clear, although there was some overlap between the level of expression measured in plants not utilizing the ubiquitin-protein fusion approach, those plants constructed with the ubiquitin-protein fusion had, on average, higher levels of expression than could be obtained without the ubiquitin fusion protein, even though the coding sequences to the protein in question were otherwise identical. The test was conducted with enough plant lines (in excess of 20 per construct) to assure that the results were significant. On average, the GUS levels were four fold higher in ubiquitin fusion plants than in comparable plants with the GUS gene alone. When comparing only high expressing lines ($\geq 200$ n moles substrate/min/mg leaf protein), the plants with the ubiquitin fusion were eight times more likely to have this high level of expression.

Northern blot analysis was done to confirm that the mRNAs encoded either the ubiquitin-GUS fusion or the GUS protein respectively. Immunoblot analysis of protein from the plant was also conducted in both experimental and control plants. The GUS gene products encoded by both sets of plants were of the same size, indicating that the ubiquitin fusion had been post-translationally processed to produce free GUS protein with ubiquitin in the plants. Similar experiments underway in rice have verified similar correct cleavage in rice plants.

While all sequences and DNA fragment sizes presented here are believed accurate, given the present state of the art occasional base pair errors are possible and may be present. The sequences and sizes are, however, quite accurate and will enable synthesis and manipulation of functional gene constructions in accordance with the methods described here.

We claim:

1. A vector to express a desired protein in plants, the vector comprising, 5' to 3':

a promoter effective in plant cells;

a protein coding sequence including a first sequence encoding a UBQ11 ubiquitin repeat domain and a second sequence encoding the desired protein, the desired protein not being ubiguitin, the first and second sequence arranged to encode a ubiquitin-protein fusion; and a transcriptional terminator effective in plants.

2. A vector as claimed in claim 1 wherein the second sequence encoding the desired protein is located immediately 3' to the carboxyl terminal residue of the UBQ11 repeat domain encoding sequence.

3. A vector as claimed in claim 2 wherein the second sequence has the codon for the protein at its amino terminus altered to encode an amino acid other than methionine.

4. A vector as claimed in claim 1 wherein the promoter is the cauliflower mosaic virus 35S promoter.

5. A vector as claimed in claim 1 wherein the first sequence is SEQ ID. NO. 1.

6. A plant cell comprising within its genome a stably incorporated portion of the vector of claim 1 including the promoter, the protein coding sequence and the transcriptional terminator, and further containing the desired protein free of the ubiquitin.

7. Plant seeds comprising in their genome the vector of claim 1.

8. A method of expressing a protein in the cells of an angiosperm plant comprising the steps of:

(a) constructing a plant expression vector including a promoter effective in plant cells, a protein coding sequence including both a first sequence encoding a UBQ11 ubiquitin repeat domain and a second sequence encoding the protein so that a ubiquitin-protein fusion is encoded, the protein encoded by the second sequence not being ubiquitin, and a transcription termination effective in plants; and (b) transforming the vector into an angiosperm plant.

* * * * *

UNITED STATES PATENT AND TRADEMARK OFFICE
CERTIFICATE OF CORRECTION

PATENT NO. : 5,773,705
DATED : June 30, 1998
INVENTOR(S) : Richard D. Vierstra, David Hondred, Judy Callis It is certified that error appears in the above-identified patent and that said Letters Patent is hereby corrected as shown below:

Column 1, line 5:

--This invention was made with United States Government Support awarded by the following agencies: USDA Grant No. CR60-88-37262-3368. The United States Government has certain rights in this invention.--

Signed and Sealed this

Eighth Day of September, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 231 base pairs
        ( B ) TYPE: nucleic acid
        ( C ) STRANDEDNESS: double
        ( D ) TOPOLOGY: linear     ( i i ) MOLECULE TYPE: cDNA to mRNA     ( i i i ) HYPOTHETICAL: NO     ( i v ) ANTI-SENSE: NO     ( v ) FRAGMENT TYPE: C-terminal     ( v i ) ORIGINAL SOURCE:
        ( A ) ORGANISM: Arabidopsis thaliana     ( v i i ) IMMEDIATE SOURCE:
        ( B ) CLONE: UBQ11

( x i ) SEQUENCE DESCRIPTION: SEQ ID NO:1:

```
ATGCAGATCT   TCGTAAAGAC   TTTGACCGGA   AAGACCATCA   CTCTTGAAGT   TGAGAGCTCC        60

GACACCATTG   ATAACGTGAA   GGCTAAGATC   CAGGACAAGG   AAGGCATTCC   TCCGGACCAG       120

CAGCGTCTCA   TCTTCGCTGG   AAAGCAGCTT   GAGGATGGAC   GTACTTTGGC   CGACTACAAC       180

ATCCAGAAGG   AGTCTACTCT   TCACTTGGTC   CTCCGTCTCC   GTGGTGGTTT   C                231
```

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear     ( i i ) MOLECULE TYPE: other nucleic acid     ( i i i ) HYPOTHETICAL: NO     ( i v ) ANTI-SENSE: NO     ( v i i ) IMMEDIATE SOURCE:
        ( B ) CLONE: 35S-NH2

( i x ) FEATURE:
        ( A ) NAME/KEY: misc_feature
        ( B ) LOCATION: 1..5
        ( D ) OTHER INFORMATION: /function="Sal I restriction site"

( i x ) FEATURE:
        ( A ) NAME/KEY: misc_feature
        ( B ) LOCATION: 6..11
        ( D ) OTHER INFORMATION: /function="Nhe I restriction site"

( i x ) FEATURE:

(A) NAME/KEY: misc_feature
                (B) LOCATION: 12..17
                (D) OTHER INFORMATION: /function="Eag I restriction site"

(ix) FEATURE:
                (A) NAME/KEY: misc_feature
                (B) LOCATION: 18..22
                (D) OTHER INFORMATION: /function="Apa I restriction site"

(ix) FEATURE:
                (A) NAME/KEY: misc_feature
                (B) LOCATION: complement (5..18)
                (D) OTHER INFORMATION: /function="Complementary strand"

(xi) SEQUENCE DESCRIPTION: SEQ ID NO:2:

TCGACGCTAG CCGGCCGGGG CC                                                                                22

(2) INFORMATION FOR SEQ ID NO:3:

(i) SEQUENCE CHARACTERISTICS:
                (A) LENGTH: 161 base pairs
                (B) TYPE: nucleic acid
                (C) STRANDEDNESS: double
                (D) TOPOLOGY: linear (ii) MOLECULE TYPE: other nucleic acid (iii) HYPOTHETICAL: NO (iv) ANTI-SENSE: NO (vii) IMMEDIATE SOURCE:
                (B) CLONE: UBQ-BT (ix) FEATURE:
                (A) NAME/KEY: misc_feature
                (B) LOCATION: 4..9
                (D) OTHER INFORMATION: /function="Hind III restriction
                        site"

(ix) FEATURE:
                (A) NAME/KEY: misc_feature
                (B) LOCATION: 47..52
                (D) OTHER INFORMATION: /function="Bgl II restriction
                        site"

(ix) FEATURE:
                (A) NAME/KEY: misc_feature
                (B) LOCATION: 58..64
                (D) OTHER INFORMATION: /product="Eae I restriction site"

(ix) FEATURE:
                (A) NAME/KEY: misc_feature
                (B) LOCATION: 110..116
                (D) OTHER INFORMATION: /function="Sac II restriction
                        site"

(ix) FEATURE:
                (A) NAME/KEY: misc_feature
                (B) LOCATION: 146..152
                (D) OTHER INFORMATION: /function="Nsi I restriction site"

(ix) FEATURE:
                (A) NAME/KEY: misc_feature
                (B) LOCATION: 153..158
                (D) OTHER INFORMATION: /function="Sal I restriction site"

(xi) SEQUENCE DESCRIPTION: SEQ ID NO:3:

GGGAAGCTTT TTATTTTAA TTTTCTTTCA AATACTTCCA CCATGCAGAT CTTCCTCCTG                                         60

GCCGACTACA ACATCCAGAA GGAGTCTACT CTTCACTTGG TCCTCCGTCT CCGCGGTGGT                                       120

ATGGAGAACA ATCCGAACAT CAATGAATGC ATGTCGACCC C                                                          161

(2) INFORMATION FOR SEQ ID NO:4:

(i) SEQUENCE CHARACTERISTICS:
  (A) LENGTH: 117 base pairs
  (B) TYPE: nucleic acid
  (C) STRANDEDNESS: double
  (D) TOPOLOGY: linear (ii) MOLECULE TYPE: other nucleic acid (iii) HYPOTHETICAL: NO (iv) ANTI-SENSE: NO (vii) IMMEDIATE SOURCE:
  (B) CLONE: UBQ-GUS (ix) FEATURE:
  (A) NAME/KEY: misc_feature
  (B) LOCATION: 4..9
  (D) OTHER INFORMATION: /function="Sac II restriction site"

(ix) FEATURE:
  (A) NAME/KEY: misc_feature
  (B) LOCATION: 39..44
  (D) OTHER INFORMATION: /function="Xho I restriction site"

(ix) FEATURE:
  (A) NAME/KEY: misc_feature
  (B) LOCATION: 103..108
  (D) OTHER INFORMATION: /function="Bcl I restriction site"

(ix) FEATURE:
  (A) NAME/KEY: misc_feature
  (B) LOCATION: 109..114
  (D) OTHER INFORMATION: /function="Xba I restriction site"

(xi) SEQUENCE DESCRIPTION: SEQ ID NO:4:

```
GGGCCGCGGT GGTATGTTAC GTCCTGTAGA AACCCCAACT CGAGAAATCA AAAAACTCGA    60
CGGCCTGTGG GCATTCAGTC TGGATCGCGA AAACTGTGGA ATTGATCATC TAGACCC      117
```

(2) INFORMATION FOR SEQ ID NO:5:

(i) SEQUENCE CHARACTERISTICS:
  (A) LENGTH: 831 base pairs
  (B) TYPE: nucleic acid
  (C) STRANDEDNESS: double
  (D) TOPOLOGY: linear (ii) MOLECULE TYPE: other nucleic acid (iii) HYPOTHETICAL: NO (iv) ANTI-SENSE: NO (vii) IMMEDIATE SOURCE:
  (B) CLONE: 35S/AMV/UBQ11/UBQ-GUS (ix) FEATURE:
  (A) NAME/KEY: CDS
  (B) LOCATION: 503..730

(ix) FEATURE:
  (A) NAME/KEY: promoter
  (B) LOCATION: 1..502

(ix) FEATURE:
  (A) NAME/KEY: misc_feature
  (B) LOCATION: 1..6
  (D) OTHER INFORMATION: /function="Eco RI restriction site"

(ix) FEATURE:
  (A) NAME/KEY: misc_feature
  (B) LOCATION: 7..12
  (D) OTHER INFORMATION: /function="Sac I restriction site"

(ix) FEATURE:

(A) NAME/KEY: misc_feature
(B) LOCATION: 13..18
(D) OTHER INFORMATION: /function="Kpn I restriction site"

(ix) FEATURE:
(A) NAME/KEY: misc_feature
(B) LOCATION: 18..24
(D) OTHER INFORMATION: /function="Apa I restriction site"

(ix) FEATURE:
(A) NAME/KEY: misc_feature
(B) LOCATION: 464..469
(D) OTHER INFORMATION: /function="Hind III restriction site"

(ix) FEATURE:
(A) NAME/KEY: misc_feature
(B) LOCATION: 720..726
(D) OTHER INFORMATION: /function="Sac II restriction site"

(ix) FEATURE:
(A) NAME/KEY: misc_feature
(B) LOCATION: 819..825
(D) OTHER INFORMATION: /function="Bcl I restriction site"

(ix) FEATURE:
(A) NAME/KEY: misc_feature
(B) LOCATION: 826..831
(D) OTHER INFORMATION: /function="Xba I restriction site"

(xi) SEQUENCE DESCRIPTION: SEQ ID NO:5:

```
GAATTCGAGC TCGGTACCGG GCCCCGGCCG GCTAGCGTCG AGGAACATGG TGGAGCACGA      60

CACTCTCGTC TACTCCAAGA ATATCAAAGA TACAGTCTCA GAAGACCAAA GGGCTATTGA     120

GACTTTTCAA CAAAGGGTAA TATCGGGAAA CCTCCTCGGA TTCCATTGCC CAGCTATCTG     180

TCACTTCATC AAAAGGACAG TAGAAAAGGA AGGTGGCACC TACAAATGCC ATCATTGCGA     240

TAAAGGAAAG GCTATCGTTC AAGATGCCTC TGCCGACAGT GGTCCCAAAG ATGGACCCCC     300

ACCCACGAGG AGCATCGTGG AAAAAGAAGA CGTTCCAACC ACGTCTTCAA AGCAAGTGGA     360

TTGATGTGAT ATCTCCACTG ACGTAAGGGA TGACGCACAA TCCCACTATC CTTCGCAAGA     420

CCCTTCCTCT ATATAAGGAA GTTCATTTCA TTTGGAGAGG ACCAAGCTTT TTATTTTAA     480

TTTTCTTTCA AATACTTCCA CC ATG CAG ATC TTC GTA AAG ACT TTG ACC GGA     532
                           Met Gln Ile Phe Val Lys Thr Leu Thr Gly
                            1               5                    10

AAG ACC ATC ACT CTT GAA GTT GAG AGC TCC GAC ACC ATT GAT AAC GTG     580
Lys Thr Ile Thr Leu Glu Val Glu Ser Ser Asp Thr Ile Asp Asn Val
             15                  20                  25

AAG GCT AAG ATC CAG GAC AAG GAA GGC ATT CCT CCG GAC CAG CAG CGT     628
Lys Ala Lys Ile Gln Asp Lys Glu Gly Ile Pro Pro Asp Gln Gln Arg
         30                  35                  40

CTC ATC TTC GCT GGA AAG CAG CTT GAG GAT GGA CGT ACT TTG GCC GAC     676
Leu Ile Phe Ala Gly Lys Gln Leu Glu Asp Gly Arg Thr Leu Ala Asp
     45                  50                  55

TAC AAC ATC CAG AAG GAG TCT ACT CTT CAC TTG GTC CTC CGT CTC CGC     724
Tyr Asn Ile Gln Lys Glu Ser Thr Leu His Leu Val Leu Arg Leu Arg
 60                  65                  70

GGT GGT ATGTTACGTC CTGTAGAAAC CCCAACTCGA GAAATCAAAA AACTCGACGG     780
Gly Gly
 75

CCTGTGGGCA TTCAGTCTGG ATCGCGAAAA CTGTGGAATT GATCATCTAG A             831
```

(2) INFORMATION FOR SEQ ID NO:6:

(i) SEQUENCE CHARACTERISTICS:
(A) LENGTH: 76 amino acids (B) TYPE: amino acid
(D) TOPOLOGY: linear (ii) MOLECULE TYPE: protein (xi) SEQUENCE DESCRIPTION: SEQ ID NO:6:

| Met | Gln | Ile | Phe | Val | Lys | Thr | Leu | Thr | Gly | Lys | Thr | Ile | Thr | Leu | Glu |
|---|---|---|---|---|---|---|---|---|---|---|---|---|---|---|---|
| 1 | | | | 5 | | | | | 10 | | | | | 15 | |
| Val | Glu | Ser | Ser | Asp | Thr | Ile | Asp | Asn | Val | Lys | Ala | Lys | Ile | Gln | Asp |
| | | | 20 | | | | | 25 | | | | | 30 | | |
| Lys | Glu | Gly | Ile | Pro | Pro | Asp | Gln | Gln | Arg | Leu | Ile | Phe | Ala | Gly | Lys |
| | | 35 | | | | | 40 | | | | | 45 | | | |
| Gln | Leu | Glu | Asp | Gly | Arg | Thr | Leu | Ala | Asp | Tyr | Asn | Ile | Gln | Lys | Glu |
| | 50 | | | | | 55 | | | | | 60 | | | | |
| Ser | Thr | Leu | His | Leu | Val | Leu | Arg | Leu | Arg | Gly | Gly | | | | |
| 65 | | | | 70 | | | | | 75 | | | | | | |